United States Patent
Beruto et al.

(10) Patent No.: US 7,332,113 B2
(45) Date of Patent: Feb. 19, 2008

(54) METHOD FOR THE PRODUCTION OF A BIOCOMPATIBLE POLYMER-CERAMIC COMPOSITE MATERIAL WITH A PREDETERMINED POROSITY

(75) Inventors: Dario Beruto, Genoa (IT); Rodolfo Botter, Genoa (IT); Leonardo Albanese, Genoa (IT); Pierfrancesco Robotti, Torbole sul Garda (IT); Giovanni Calonego, Legnago (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 643 days.

(21) Appl. No.: 10/466,703

(22) PCT Filed: Jan. 18, 2002

(86) PCT No.: PCT/IT02/00030

§ 371 (c)(1),
(2), (4) Date: Jan. 22, 2004

(87) PCT Pub. No.: WO02/056928

PCT Pub. Date: Jul. 25, 2002

(65) Prior Publication Data

US 2004/0129650 A1    Jul. 8, 2004

(30) Foreign Application Priority Data

Jan. 18, 2001   (IT)   .............................. MI01A0089

(51) Int. Cl.
   *B29C 41/04*   (2006.01)
(52) U.S. Cl. ...................... 264/42; 264/45.7; 264/311; 264/344; 424/423
(58) Field of Classification Search .................. 264/42, 264/311, 319, 45.7, 344; 424/423
   See application file for complete search history.

(56) References Cited

U.S. PATENT DOCUMENTS

| | | | | | |
|---|---|---|---|---|---|
| 4,373,217 | A | * | 2/1983 | Draenert | .................. 623/23.62 |
| 4,610,693 | A | * | 9/1986 | Niwa et al. | ............... 623/11.11 |
| 4,778,834 | A | * | 10/1988 | Murray | ........................ 523/212 |
| 4,973,168 | A | * | 11/1990 | Chan | ........................... 366/139 |
| 5,470,803 | A | * | 11/1995 | Bonfield et al. | ............... 501/1 |
| 5,993,716 | A | * | 11/1999 | Draenert | ..................... 264/221 |
| 6,599,516 | B1 | * | 7/2003 | Knaack | ....................... 424/423 |

* cited by examiner

*Primary Examiner*—Allan R. Kuhns
(74) *Attorney, Agent, or Firm*—Ladas and Parry LLP

(57) ABSTRACT

Method for the production of a biocompatible polymer-ceramic composite material with a predetermined porosity, designed and determined a priori, which includes a first phase (a) of the production of a suspension of a bioceramic material in distilled water, a second phase (b) in the which a compact of the bioceramic material containing a desired quantity of water is obtained from the suspension, and a third phase (c) in the which the compact is mixed with a polymeric material and/or a liquid monomer.

2 Claims, 5 Drawing Sheets water retained by the compacts/acceleration of the centrifuge (Xg)

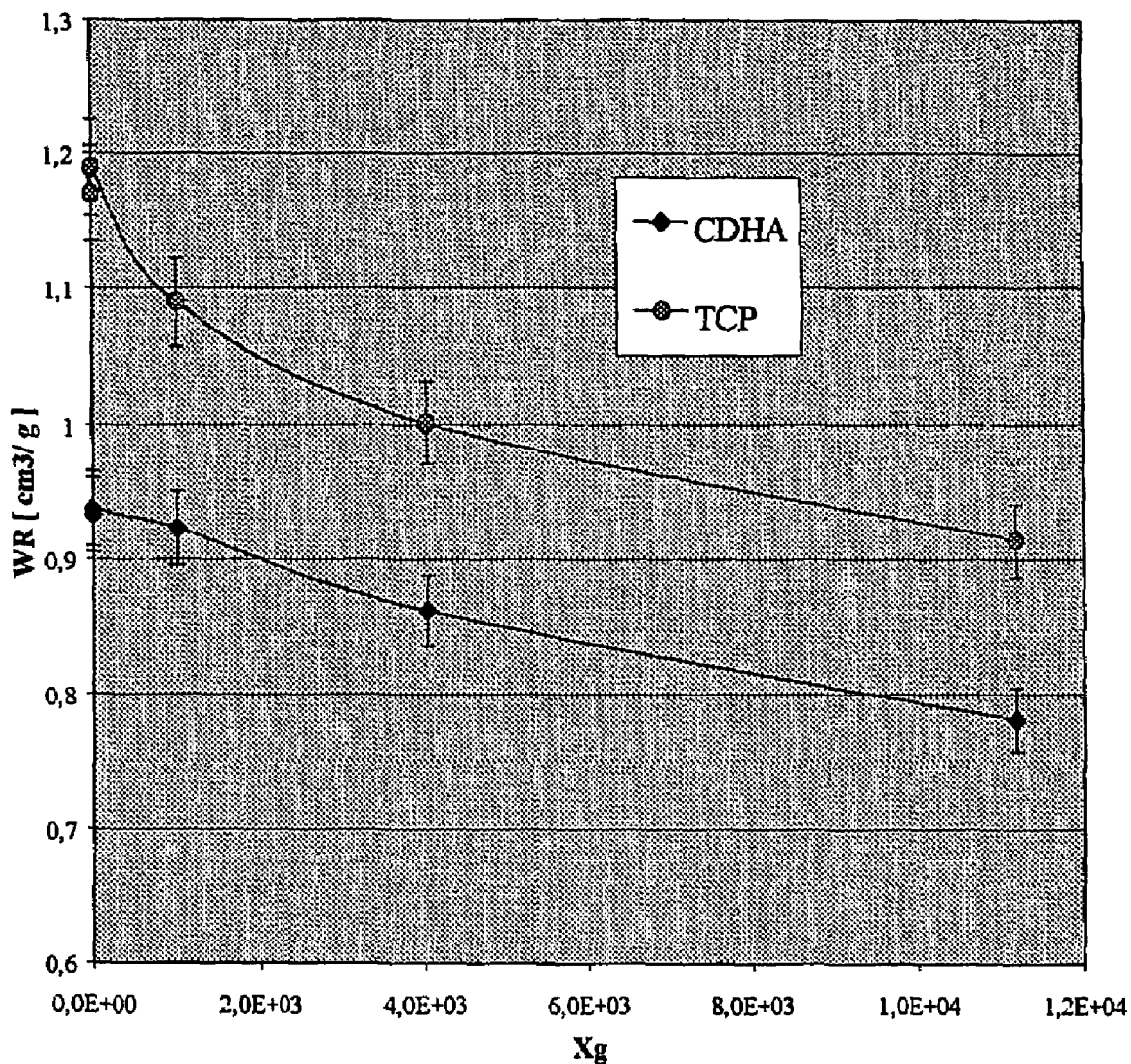
Fig. 1: water retained by the compacts/acceleration of the centrifuge (Xg)

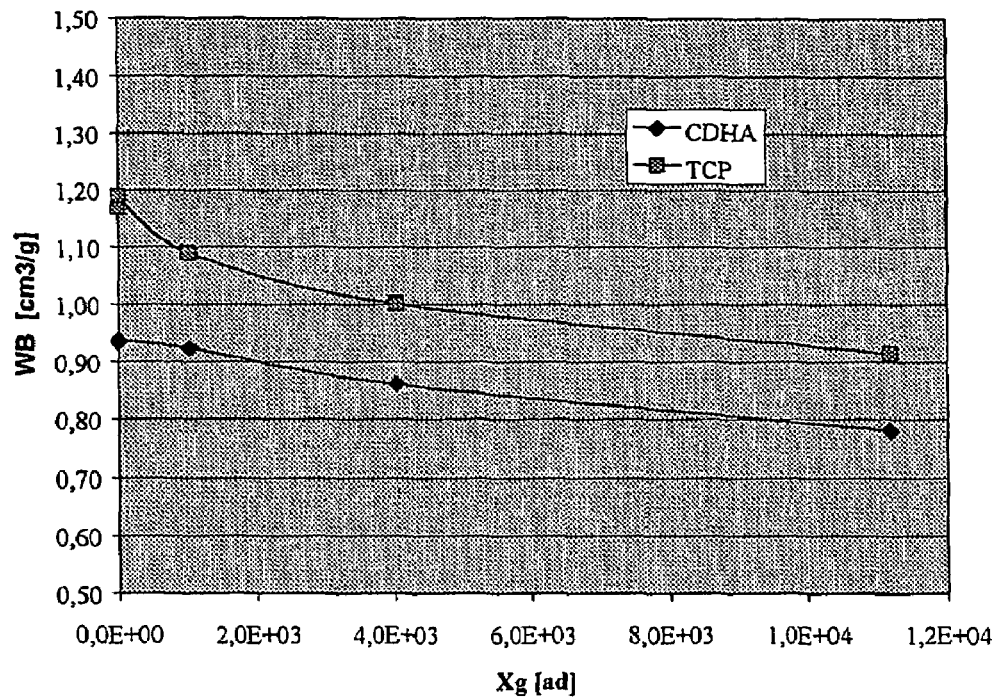
Fig. 2: bonded water retained by the compacts/acceleration of the centrifuge (Xg)
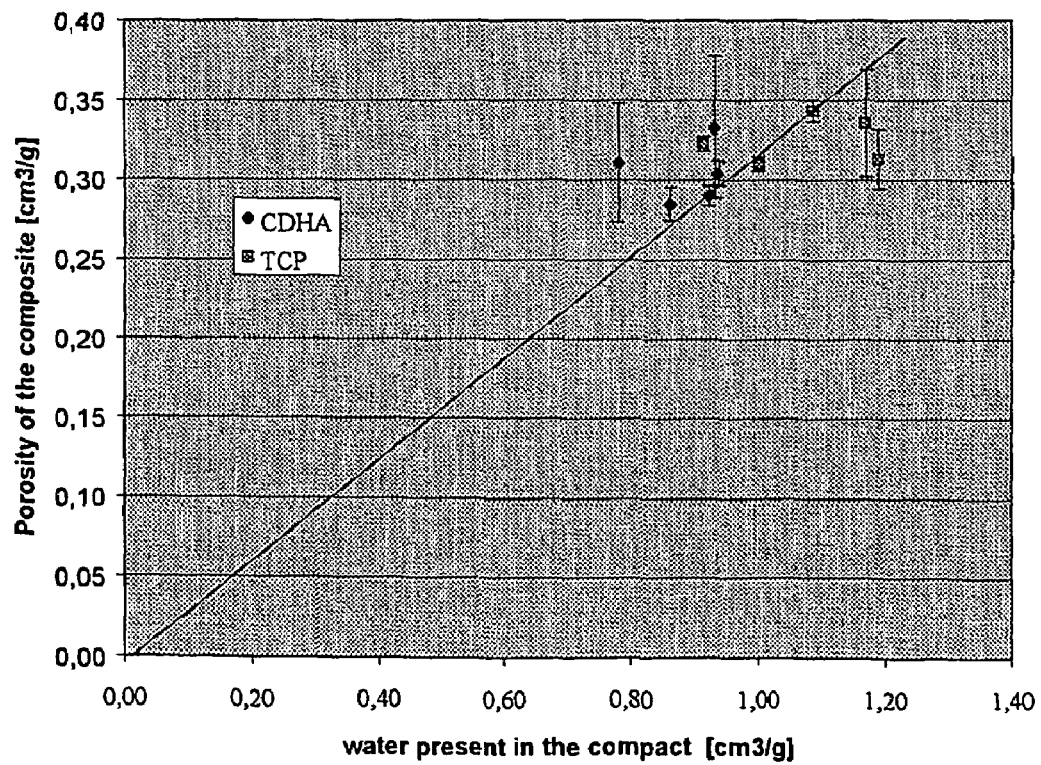
Fig. 3: porosity of the composite/water present in the compact

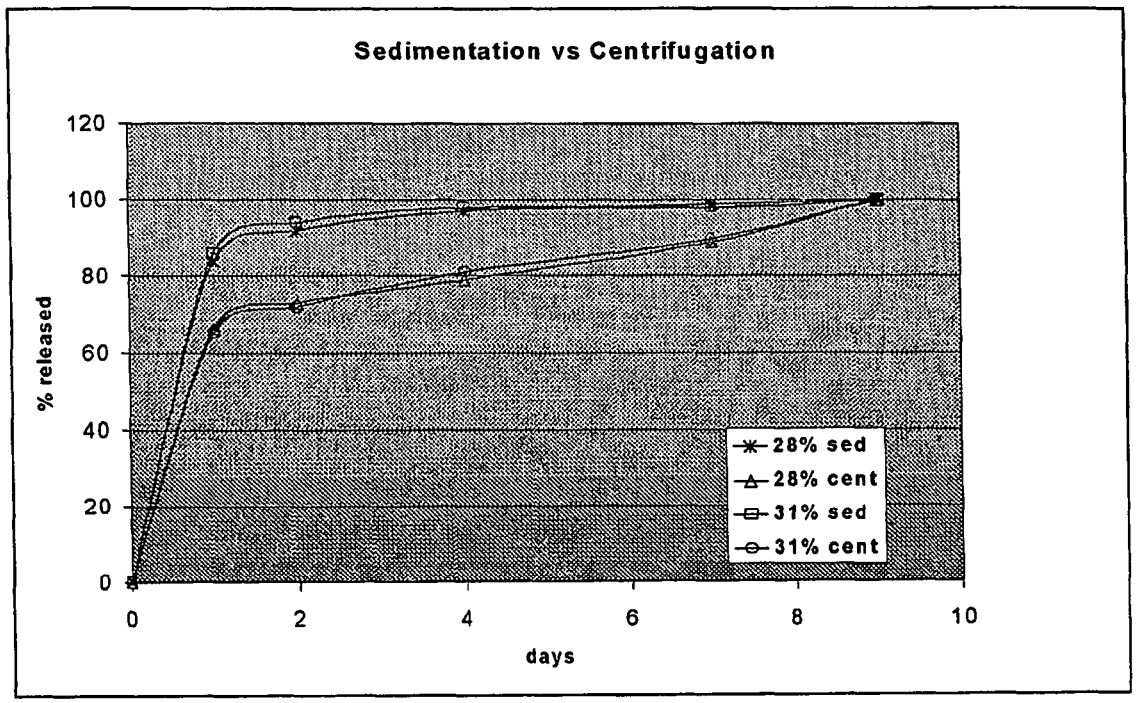
Fig. 4: Kinetic curve of the release of antibiotic from composite PMMA/α-TCP sedimented and centrifugated
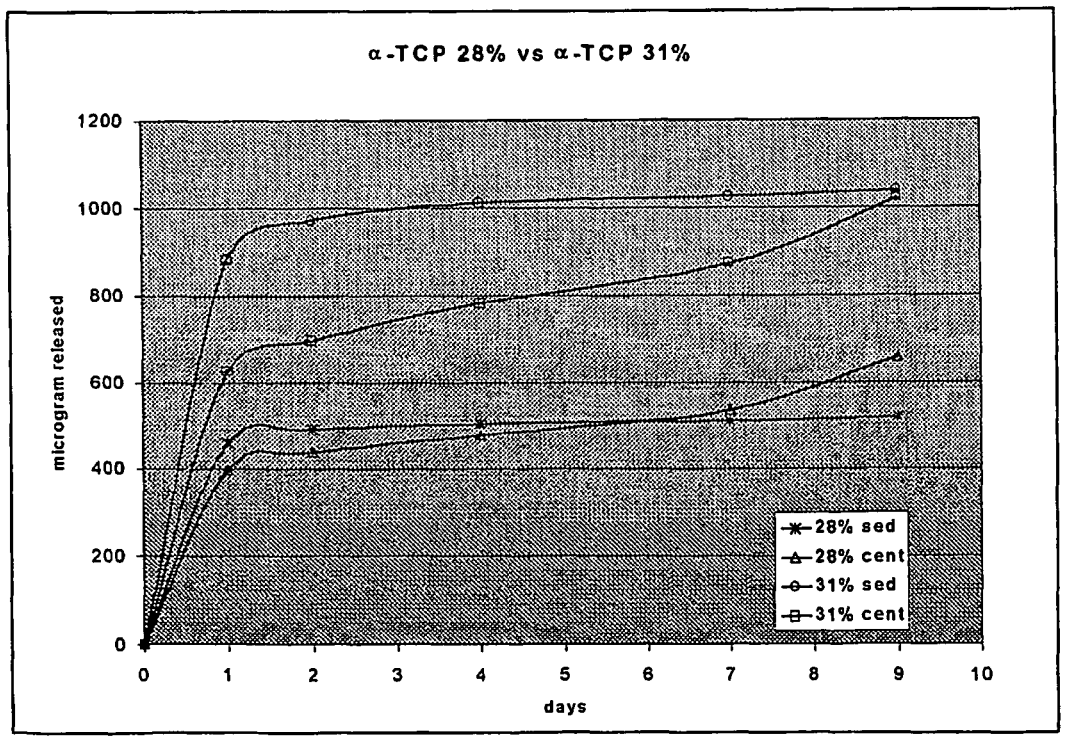
Fig. 5: Quantitative release of antibiotic from composite PMMA/α-TCP sedimented and centrifugated

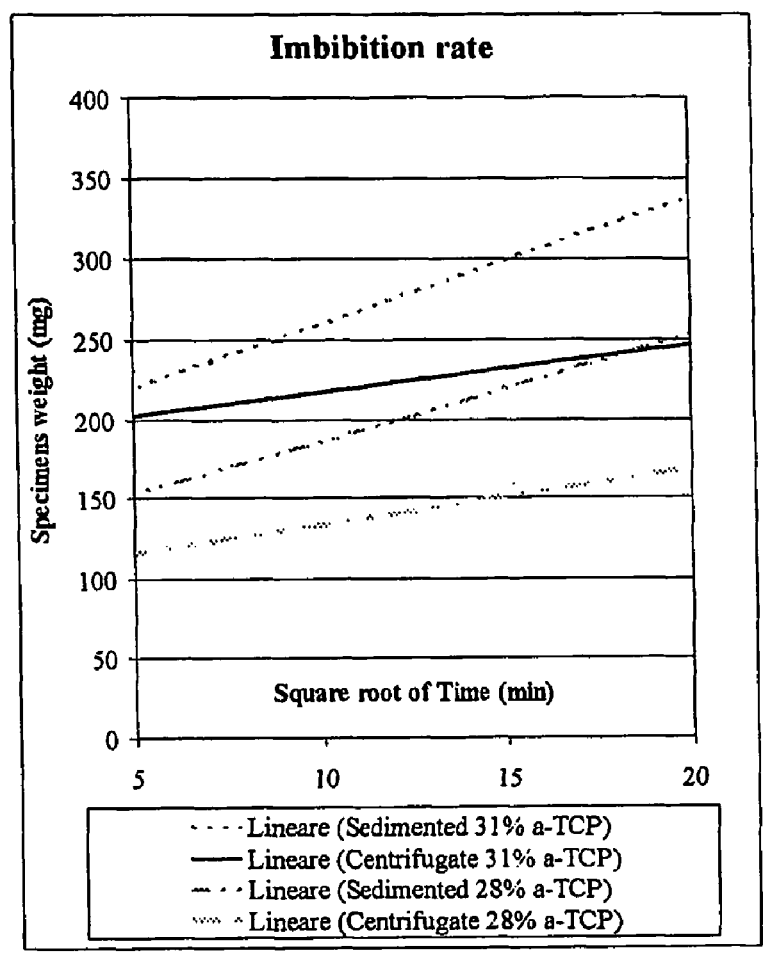
Fig. 6: Imbibition rate of water by Wicking Technique in composite PMMA/α-TCP

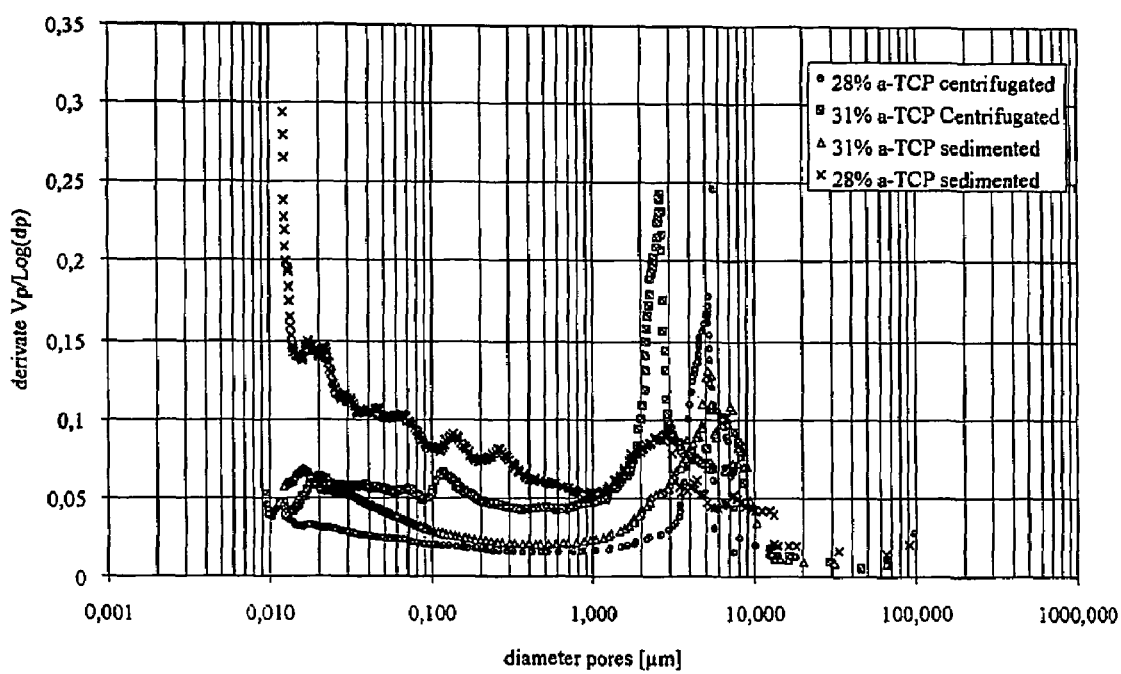
Fig. 7: Pores diameters for composite PMMA/α-TCP
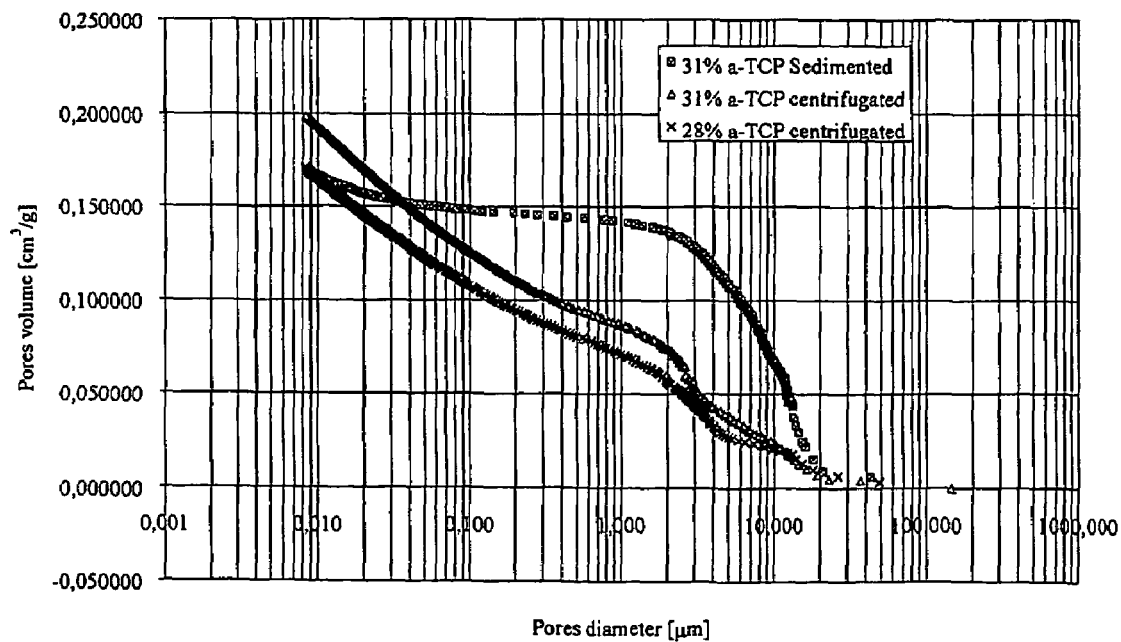
Fig. 8: Pores Volume for composite PMMA/α-TCP

METHOD FOR THE PRODUCTION OF A BIOCOMPATIBLE POLYMER-CERAMIC COMPOSITE MATERIAL WITH A PREDETERMINED POROSITY

TECHNICAL FIELD

The present invention relates to a method used to obtain a biocompatible polymer-ceramic composite material of a predetermined porosity, designed and determined a priori.

BACKGROUND ART

It has been known for some time that polymethyl methacrylate (PMMA)/calcium phosphate type porous composites may be employed in a series of applications, such as the filling of bone voids or as drug delivery systems for the controlled release of pharmaceuticals. In fact, these composites display a proven biocompatibility, and at the same time they succeed in wedding the mechanical resistance characteristics inherent in the polymeric materials such as PMMA with the bio-reabsorption characteristics of bioceramic materials such as calcium phosphate.

A determining aspect of such polymer-ceramic composite materials is porosity, which can be a deciding factor both for the mechanical characteristics and for the functional characteristics of the composite materials themselves. In fact, porosity allows the composite material to host staminal cells, proteins that stimulate the colonisation of the patient's staminal cells, antibiotics, growth elements, and other bioactive substances that in general promote the processes of attachment, osteointegration and/or reabsorption of the composite material.

Further, designing the porosity is particularly important, since the pores must assume specific characteristics both in shape and size as a function of the various applications of the material. In fact, the role of porosity and the degree of interconnection between the pores has been recognised as an important parameter both for the reconstruction of bone tissue inside the implanted polymer matrix and for the release periods of any pharmaceuticals inserted in the composite material.

Generally, biopolymeric porous materials are created using foaming agents or by inserting in the polymer matrix powders of particles that can be dissolved at a later stage, as, for example, soluble salts or gelatin microspheres.

The solid particles destined to create the porosity can be introduced in the melted polymer, in the monomer or mixed with the solid prepolymer before the polymerisation or reticulation reaction. During this phase, difficulties may arise due to the possibility that a few particles can remain isolated and therefore do not contribute to the formation of porosity, or that the area of contact between two particles can be very small. In such cases, the periods for the removal of the solid increase, the diffusion of bodily fluids is inhibited and a large fraction of porosity can therefore prove useless from the point of view of cellular colonisation. Porosity created using foaming agents can also entail the same type of difficulty, with the formation of a large fraction of cells that are closed or only virtually connected through fractures in the surfaces that connect one cell to another.

With the aim of resolving these difficulties, the use of biocompatible and bioabsorbable liquids has been proposed. In particular, an especially effective method according to U.S. Pat. No. 4,373,217 is the advance treatment of the ceramic material powders with these liquids, aiming to fill the porosity, at least in part, in order to avoid it becoming filled with monomer during the initial phases of polymerisation, consequently impeding the subsequent dissolution of the ceramic material and therefore the creation of the desired porosity in the final composite. Further, the article "*Use of α-tricalcium phosphate (TPC) . . .*" by D. T. Beruto, R, Botter in the Journal of Biomedical Materials Research 49, 498-505, 2000, discloses the use of distilled water to create aqueous dispersions of the bioceramic material utilised, which are subsequently mixed with the polymeric material and with liquid monomer. The use of these dispersions, beyond avoiding the difficulties explained above and guaranteeing the generation of good porosity, also prevents the bioceramic materials used, as for example calcium phosphate, from absorbing part of the liquid monomer and removing it from polymerisation with the successive risk that it be released itself in the patient's circulatory system. The liquids utilised, in fact, being miscible with the bioceramic material and non-miscible with the monomer or with the polymer used, impede the contact of the latter with the bioceramic material itself.

The techniques utilised up to now, which call for the creation of aqueous dispersions of the bioceramic material, notwithstanding the fact that they succeed in resolving the difficulties described above, are nonetheless incapable of allowing for the design and achievement of a final porosity of the predetermined composite.

DISCLOSURE OF INVENTION

The aim of the present invention is to realise a method for the production of a polymer-ceramic composite material using which it will be possible to predict and design the porosity of the final composite material.

According to the invention therefore, a method is created to obtain a biocompatible polymer-ceramic composite material of a predetermined porosity, said method comprising a first phase (a) of the production of a suspension of bioceramic material in distilled water, and is characterised by the fact that it also comprises a second phase (b) in which a compact of said bioceramic material containing a desired quantity of water is obtained from the suspension; said compact is then mixed in a third phase (c) with a polymeric material and/or with a liquid monomer.

Preferably, the desired quantity of water is calculated on the basis of a combination of a calibration curve of the water contained in a compact of bioceramic material as a function of the different level of compaction used to create the compact, and from a calibration curve of the porosity of a polymer-ceramic composite as a function of the quantity of water contained in the compact used in creating the polymer-ceramic composite itself.

Preferably, the compact is obtained using a sedimentation in centrifuge operation.

Preferably, the polymeric material utilised is polymethyl methacrylate, the liquid monomer is methyl methacrylate and a suspension of a prepolymer in the monomer is prepared in advance, which is then mixed with the compact containing the predetermined quantity of water.

Preferably, the bioceramic material is constituted of calcium-deficient hydroxyapatite or tricalcic-phosphate $\alpha$.

Preferably the bioceramic material should be used with a defined granulometry. For instance, diameters between 1 μm and 200 μm can be used.

More Preferably the diameter range for the selected powder can be comprised between 1 μm and 10 μm or 10 μm and 50 μm or 50 μm and 100 μm.

According to a preferred embodiment of the invention, the preparation of the tricalcic-phosphate α comprises a final rapid cooling phase and a sieving phase, possibly after grinding, in order to collect particles of irregular shape, approximately ranging between 1 μm and 10 μm in size.

BRIEF DESCRIPTION OF THE DRAWINGS

Further characteristics of the invention will be apparent from the following description of a few examples, provided for illustrative purposes only and that are not limitative, and which will be described with reference to the attached figures, among others, in which:

FIG. 1 is a graphic that shows the trend of the total volume WR of water retained by the compact at the end of the sedimentation trials as a function of the centrifugal acceleration used;

FIG. 2 is a graphic that represents the trend of the volume WB of bonded water retained by the compact at the end of the sedimentation trials, as a function of the centrifugal acceleration used; and FIG. 3 is a graphic which represents the trend of the porosity of the polymer-ceramic composite as a function of the water retained by the compact used in the production of the composite itself.

FIGS. 4 and 5 are comparative graphics representing the quantitative release of an antibiotic from composite PMMA/α-TPC sedimented and centrifuged;

FIG. 6 shows the imbibition rate of water by Wicking Technique composite PMMA/α-TPC;

FIGS. 7 and 8 shows the pores diameters and volumes for composite PMMA/α-TPC obtained according to the invention.

BEST MODE FOR CARRYING OUT THE INVENTION

EXAMPLES

Two series of composites, A and B, were prepared, which are distinguished from each other by the use of two different bioceramic materials with the aim of highlighting how the design of the porosity also depends on the type of bioceramic material utilised. Specifically, the series of composites indicated by the letter A calls for the use of tricalcic-phosphate α (α-TCP), while the series of composites indicated with a B calls for the use of calcium-deficient hydroxyapatite (CDHA).

In particular, in the examples shown below, the design and prediction of the porosity of the biocompatible polymer-ceramic composite material was obtained using a method including the following phases:

(a') producing a suspension of a bioceramic material, with a selected granulometry, in distilled water;

(b') starting from identical volumetric quantities of initial suspension, obtaining from the suspension a series of compacts of the bioceramic material containing different quantities of water;

(c') mixing each of the compacts thus obtained with an identical quantity of a polymeric material and/or a liquid monomer in order to obtain a porous geometric solid of pre-defined dimensions;

(d') for each compact, calculating the porosity of the solid obtained from it; and (e') correlating the porosity with the residual water content of the compact.

Example 1

Series of Composites A

Example 1a

Preparation of the Compacts

An inorganic tricalcic-phosphate salt α (α-TCP) was prepared using a reaction in the solid state between anhydrous $CaCO_3$ and $CaHPO_4$. After mixing, the dibasic calcium phosphate powders were heated in a muffle kiln to 1573 K and at the end of the reaction were rapidly cooled in order to stabilize the α phase. After cooling, the powder was sieved using a 60 mesh sieve, and the fraction of powder that passed through the sieve was analyzed with X-ray diffraction, confirming the α structure of the powder. The average size of the grains was approximately 10 micron.

The inorganic salt α-TCP was dispersed in the aqueous phase with a solid phase volumetric concentration equal to 10%. From the dispersions thus obtained, a total volume equal to 12.7 $cm^3$ was extracted. This volume was treated in a centrifuge and subjected for a pre-defined period of 15 minutes to a value of acceleration (Xg). The same procedure was repeated various times, subjecting the various dispersions obtained to various values of acceleration (Xg). At the end of each centrifugation period, a "compact" and an aqueous phase were obtained. For each compact obtained, the aqueous phase was separated from the compact and the residual water content of the compact was determined by weight. FIG. 1 shows the water content WR (expressed in $cm^3$/grams of dry powder) remaining in the various compacts obtained for different values of Xg.

The water content WR is formed by water still relatively free between the cracks in the grains and by water bonded by capillary and superficial forces to the inorganic matrix. According to this invention, the major datum in predicting the final porosity of the composite is nonetheless not total water WR, but water WB that is bonded by forces of various natures to the ceramic matrix. This quantity is defined by:

$$WB = WR \times p1 \qquad (1)$$

where, for every Xg, WR is the total water inside the compact, WB is the bonded water and p1 is the probability that the water is bonded. This probability is complementary to the probability of finding free water. The fraction of free water inside each compact therefore represents that part of the water that is susceptible to leak from the ceramic matrix under mild force. When a specific compact, obtained by treating the dispersion to an Xg acceleration, is subjected to a further force of dXg, the first water to exit the ceramic matrix will be the least bonded portion. An index of this quantity is given by the value of the derivative of the curve in FIG. 3 calculated for each experimental abscissa Xg. Therefore, a reasonable formula to use in calculating WB is:

$$WB = WR \times [1 - k(dWB/dXg)] \qquad (2)$$

where k is a parameter chosen as a function of the dispersion of the experimental data in order to optimize the linearity of the relation.

FIG. 2 illustrates the results of the calculations performed as above on the basis of the experimental results of FIG. 1, in order to evaluate the bonded water content WB corresponding to each experimental content WR.

Example 1b

Preparation of the Composites

The composites (PMMA/phosphate) were produced using pre-polymerized PMMA and monomer (MMA) powders currently on the market-such as the type used as orthopaedic cement-utilising a well-known methodology, which is summarized below.

1.33 g of monomer (MMA) were placed in a glass beaker, and to this 4 g of PMMA were added in a single solution. After approximately 10 seconds of shaking, the mixture achieved a soft, runny and homogenous consistency. A compact prepared in example 1a was added to the suspension. The resulting composite paste was rendered homogeneous by repeatedly folding the contents of the beaker back into itself for approximately 40 seconds. At the end of this operation, the content was extracted and formed between two flat plates of glass to a thickness of approximately 4 mm. After an hour at room temperature, the hardened composite was dried in an oven at 60° C. for eight hours, and subsequently was cut into regular parallelepiped shapes. Using the same procedure, various composites obtained from the different compacts prepared in example 1a were produced, as shown in Table 1, which also shows the amounts of additives (known) utilised to optimize the polymerisation reaction.

The total volume of each of the composite products was measured using helium pycnometry after drying in a vacuum at room temperature. The internal porosity (P) was determined from the difference between the apparent volume of the trial (Va) determined geometrically and the real volume (Vr) determined with the pycnometer.

$$P = Va - Vr$$

FIG. 3 shows the porosity (P) of the composites as a function of the water content (expressed in $cm^3$/grams of powder) remaining in the various compacts from which the composites themselves were obtained.

Example 2

Series of Composites B

Example 2a

Preparation of the Compact

The procedure described in example 1a was repeated with the difference that the inorganic salt used, rather than α-TCP, was calcium-deficient hydroxyapatite (CDHA).

As in example 1a, FIG. 1 shows the water content (expressed in $cm^3$/grams of dry powder) remaining in the various compacts obtained at different values of Xg, and FIG. 2 contains the corresponding values of WB calculated as in example 1a.

Example 2b

Preparation of the Composite

The procedure described in example 1b was repeated. However, the compacts prepared in example 1b were used. The exact amounts used in terms of weight are shown in Table 1.

As for example 1b, FIG. 3 shows the porosity (P) of the composites as a function of the water content (expressed in $cm^3$/grams of powder) remaining in the various compacts from which the composites themselves were obtained.

TABLE 1

| | Component | | | |
|---|---|---|---|---|
| | PMMA 97% + 3% benzoyl peroxide | MMA 99.1% + N—N dimethyl-p-toluidine 0.9% + Hydroquinone 75 ppm | CDHA, αTCP Dry powders | Residual water |
| Quantity | 4 | 1.33 | 1.8 | From 1.4 to 2 |

Example 3

Methodology for Predicting Porosity

A very simple procedure for obtaining a desired porosity of a composite results from the examples given above. Once the desired porosity and the bioceramic material to be used have been established, using an "adjustment" graphic like the one illustrated in FIG. 3 calculated in advance for the appropriate bioceramic material, we look for the amount of water WB that the compact constituted of the bioceramic material must contain. Once the quantity of bonded water that must be contained in the compact has been established, we find the centrifugal acceleration used in preparing the compact by using a second corresponding adjustment graphic, like that illustrated in FIG. 2.

In the end it is clear that, in the event that another method of compaction is used (for example press filtering, grinding, etc.), the parameter to be considered will not be the centrifugal acceleration but a parameter inherent to the method selected.

Example 4

Methodology for Choosing an Appropriate Bioceramic Composite to Obtain a Certain Porosity In order to choose the most suitable type of commercial powder for producing a composite with PMMA of a desired porosity, we will proceed, on the basis of the previous examples, as follows:

Phase 1. Perform the calibration, in the centrifuge or with a similar technique, of the aqueous dispersions of the commercial powders under analysis;

Phase 2. Construct the graphic WB vs. Xb or other variable, according to the technique used for compaction;

Phase 3. From among the initial powders, choose that which has a water content equal to WB. If it does not exist, prepare a compact, beginning with any of the powders, subjecting the initial dispersion to the corresponding acceleration Xg according to the adjustment curve;

Phase 4. Prepare the mixture of the compact containing the desired quantity of bonded water, the pre-polymerized PMMA powders and the monomer according to the examples 2a and 2b.

Example 5

Preparation with Prepolymer Dispersions

Examples 2a and 2b are repeated using a variation of the method described, consisting in pre-mixing the PMMA prepolymer powder with the monomer to obtain a concentrated polydispersed suspension of spherical PMMA particles with an average diameter of between 15 and 40 microns and an average molecular weight of between 250,000 and 350,000 uma in a hydrophobic liquid consisting predominantly of MMA monomer. Further, we use compacts obtained by starting with bioceramic component powders with average granulometry of 10 microns that are obtained by grinding initial powders with higher granulometry, between 30 and 45 microns.

Example 6

Antibiotic Release from Preparation with Prepolymer Dispersions

2 Mixtures with the same procedure described in example 5 have been prepared. α-TCP is added in different amounts (28% and 31% w/w powder component).

Either sedimentation or centrifugation is applied.

4 different types of specimen are obtained:

28% (α-TCP Sedimented, 28% α-TCP centrifuged; 31% α-TCP Sedimented, 31% α-TCP centrifuged.

The specimen are dried for two hours at 90° C. Once dried the specimens are weighted and then immersed in an antibiotic solution (2.5% w/w gentamicin/water) for 30 mins.

The specimen are newly weighted to measure the amount of solution loaded.

Each specimen is placed in a different container with a known amount of sterile saline solution.

Takings of the saline solution are made at definite times. After each taking the saline solution is refreshed with new one.

The takings are then checked for antibiotic release using the Agar-well diffusion method.

The results show clearly that centrifugation permits to control the kinetics of release (FIG. 4); the amount of α-TCP instead influences the absolute value of antibiotic solution release (FIG. 5).

Example 7

Qualitative Control of Pore Dimensions

Mixtures with the same procedure described in example 6 have been prepared.

4 different types of specimen are obtained.

28% α-TCP Sedimented, 28% α-TCP centrifuged; 31% α-TCP Sedimented, 31% α-TCP centrifuged.

The specimen are dried for two hours at 90° C. Once dried the specimens are weighted and then immersed in mercury for porosimetry determination.

The results show that the dimensions of pores are for every mixtures comprised between 2 μm and 10 μm, with a maximum ranging between 3 μm and 5 μm. The granulometry of α-TCP (average 10 μm) influences the dimension of the pores in the matrix FIG. 7.

Example 8

Control of the Imbibition Properties for Preparation with Prepolymer Dispersions Mixtures with the same procedure described in example 6 have been prepared.

4 different types of specimen are obtained.

28% α-TCP Sedimented, 28% α-TCP centrifuged; 31% α-TCP Sedimented, 31% α-TCP centrifuged.

The specimen are dried for two hours at 90° C. Once dried the specimens are weighted and then partially immersed in distilled water for dynamic weight determination. The "Wicking technique" is applied.

The results presented in FIG. 6 show that the amount of α-TCP affects the absolute value of the water absorbed by the specimen. The centrifugation affects the speed of absorption.

Example 9

Quantitative Control of Porosity

Mixtures with the same procedure described in example 6 have been prepared.

4 different types of specimen are obtained.

28% α-TCP Sedimented, 28% α-TCP centrifuged; 31% α-TCP Sedimented, 31% α-TCP centrifuged.

The specimen are dried for two hours at 90° C. Once dried the specimen are weighted and then immersed in mercury for porosimetry determination.

The results presented in FIG. 8 show that the volume of mercury forced in the material is directly dependent on the α-TCP content and inversely dependent on centrifugation.

The results achieved are similar to the previous results, but the composites obtained also display a better interconnection in the porosity achieved, as evidenced by comparative experimentation with the composites obtained in examples 2a and 2b, performed using the "Wicking" methodology (Z. Li et al. "*Wicking technique for determination of pore size in ceramic material*", J.Am.Ceram. Soc. 77, 2220-22(1999)).

The examples described thus illustrate that the composite materials obtained using the methodology of this invention are especially well-suited both for the production of temporary prostheses with controlled release of pharmaceuticals, which can be achieved with predetermined kinetics thanks to the possibility of determining the product's porosity in advance, as well as for highly osteo-conductive bone substitutes.

Further, it is evident that using these materials, other types of applicative products can also be produced, in all cases that require a rigorous control of porosity, as, for example, with semi-permeable membranes. Finally, it is also clear that the methodology is applicable to any type of porous bioceramic material.

The invention claimed is:

1. Method for predicting and designing the porosity of a biocompatible polymer-ceramic composite material, characterized by the fact that it includes the following phases:
   (a') producing a suspension of a bioceramic material in distilled water;
   (b') starting from identical volumetric quantities of initial suspension, obtaining from the suspension a series of compacts of the selected bioceramic material containing different quantities of water;
   (c') mixing each of said compacts obtained with an identical quantity of a polymeric material and/or a liquid monomer in order to obtain a porous geometric solid of pre-defined dimensions;
   (d') for each compact, calculating the porosity of the solid by obtained from it; and
   (e') correlating said porosity with the compact's residual content in water.

2. Method for predicting and designing the porosity of a biocompatible polymer-ceramic composite material according to claim 1, characterized by the fact that the phase of obtaining said compacts, which have different residual water contents, from said suspension, is performed by centrifuging said pre-determined volumetric quantities of said suspensions at various, progressively increasing, accelerations.

* * * * *